US012773501B2

(12) United States Patent
Troebner et al.

(10) Patent No.: US 12,773,501 B2
(45) Date of Patent: Oct. 27, 2026

(54) ELECTRONIC SYSTEM FOR A DRUG DELIVERY DEVICE

(71) Applicant: Sanofi, Paris (FR)

(72) Inventors: Philipp Troebner, Frankfurt am Main (DE); Zoë Georgina Eardley, Warwick (GB); Anthony Paul Morris, Warwick (GB); William Geoffrey Arthur Marsh, Warwick (GB)

(73) Assignee: SANOFI, Paris (FR)

( * ) Notice: Subject to any disclaimer, the term of this patent is extended or adjusted under 35 U.S.C. 154(b) by 1066 days.

(21) Appl. No.: 17/914,480

(22) PCT Filed: Mar. 25, 2021

(86) PCT No.: PCT/EP2021/057670
§ 371 (c)(1),
(2) Date: Sep. 26, 2022

(87) PCT Pub. No.: WO2021/191327
PCT Pub. Date: Sep. 30, 2021

(65) Prior Publication Data

US 2023/0118732 A1 Apr. 20, 2023

(30) Foreign Application Priority Data

Mar. 27, 2020 (EP) .................................... 20315066
Jul. 23, 2020 (EP) .................................... 20315357

(51) Int. Cl.
*A61M 5/315* (2006.01)

(52) U.S. Cl.
CPC .... *A61M 5/31553* (2013.01); *A61M 5/31568* (2013.01); *A61M 5/31585* (2013.01);
(Continued)

(58) Field of Classification Search
CPC .......... A61M 5/31553; A61M 5/31568; A61M 5/31585
See application file for complete search history.

(56) References Cited

U.S. PATENT DOCUMENTS

2014/0074041 A1 3/2014 Pedersen et al.
2014/0194826 A1 * 7/2014 Nielsen .................. G16H 20/17 604/189

(Continued)

FOREIGN PATENT DOCUMENTS

EP 2729202 5/2018
JP 2015529492 A 10/2015

(Continued)

OTHER PUBLICATIONS

First Office Action, CN Patent Application No. 202180023179.0, dated Mar. 24, 2025, pp. 1-15 (with pp. 1-8 being a translation).

(Continued)

*Primary Examiner* — Dung T Ulsh
(74) *Attorney, Agent, or Firm* — Bond, Schoeneck & King, PLLC

(57) ABSTRACT

An electronic system for a drug delivery device including a dose setting and drive mechanism, a communication unit, an electronic control unit, and an electrical use detection. The dose setting and drive mechanism includes a first member and a second member that move relative to each other at least in the dose delivery operation and/or in the dose setting operation of the drug delivery device. The electronic system has a first state in which the communication unit is not activated and a second state in which the communication unit is activated. The electrical use detection unit is configured to generate a first signal indicative that the user has commenced or finished the relative movement between the first member and the second member. The electronic control (Continued)

unit is configured to switch the electronic system from the first state into the second state in response to the first signal.

19 Claims, 10 Drawing Sheets

(52) U.S. Cl.
CPC ............... *A61M 2205/3584* (2013.01); *A61M 2205/8212* (2013.01)

(56) References Cited

U.S. PATENT DOCUMENTS

| | | | | |
|---|---|---|---|---|
| 2015/0202377 | A1 | 7/2015 | Haupt | |
| 2018/0207366 | A1* | 7/2018 | Marcoz ............. | A61M 5/31568 |
| 2019/0298932 | A1 | 10/2019 | Reisenhus | |
| 2019/0321555 | A1 | 10/2019 | Biondi et al. | |
| 2020/0147317 | A1* | 5/2020 | Olesen .............. | A61M 5/31553 |

FOREIGN PATENT DOCUMENTS

| | | | |
|---|---|---|---|
| JP | 2019536573 | A1 | 12/2019 |
| WO | 2019040313 | A1 | 2/2019 |
| WO | 2020036822 | A1 | 2/2020 |
| WO | WO 2020/035406 | | 2/2020 |

OTHER PUBLICATIONS

Notice of Reasons for Rejection, JP Patent Application No. 2022-558020, dated Sep. 10, 2024, pp. 1-20 (with pp. 1-11 being a translation).

International Preliminary Report on Patentability in International Appln. No. PCT/EP2021/057670, mailed on Oct. 6, 2022, 8 pages.

International Search Report and Written Opinion in International Appln. No. PCT/EP2021/057670, mailed on Jun. 11, 2021, 10 pages.

* cited by examiner

ELECTRONIC SYSTEM FOR A DRUG DELIVERY DEVICE

CROSS-REFERENCE TO RELATED APPLICATIONS

The present application is the national stage entry of International Patent No. PCT/EP2021/057670, filed on Mar. 25, 2021, and claims priority to EP Application No. EP 20315066.9, filed on Mar. 27, 2020, and EP Application No. 20315357.2, filed on Jul. 23, 2020, the disclosures of which are incorporated herein by reference.

TECHNICAL FIELD

The present disclosure is generally directed to an electronic system for a drug delivery device. The present disclosure further relates to a drug delivery device, which preferably comprises the electronic system.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is applicable for disposable and reusable devices.

For such devices the functionality of recording doses that are dialed and delivered from the pen may be of value to a wide variety of device users as a memory aid or to support detailed logging of dose history. Thus, drug delivery devices using electronics are becoming increasingly popular in the pharmaceutical industry as well as for users or patients. For example, a drug delivery device is known from EP 2 729 202 B1 comprising an electronically controlled capturing system for capturing data related to the amount of drug expelled from a reservoir by expelling means.

WO2020/035406 A1 discloses a data collection apparatus for an injection device. Axial movement of a button at the beginning of dose dispensing is used to close an electric switch which activates the data collection apparatus. Information may be periodically transmitted to a computer via a wireless communications interface.

US 2019/0321555 A1 discloses a syringe stopper rod that comprises a sensor, a transmitter and an activation component configured to activate the sensor when the syringe stopper rod has completed a delivery stroke.

US 2014/0074041 A1 discloses a drug delivery device with a plurality of sensors detecting dose setting or dose dispensing. These sensors operate like an electrical switch by opening/closing connection to a conductive area.

However, especially if the device is designed to be self-contained, that is to say without a connector for a connection to an electrical power source which is necessary to provide electrical power for the operation of the device, the management of the resources of a power supply integrated into the device is particularly important.

SUMMARY

The present disclosure provides improvements for drug delivery devices comprising an electronic system or electronic systems for drug delivery devices.

The improvement is achieved, for example, by the subject matter defined in the independent claim. Advantageous embodiments and refinements are subject to the dependent claims. However, it should be noted that the disclosure is not restricted to the subject matter defined in the appended claims. Rather, the disclosure may comprise improvements in addition or as an alternative to the ones defined in the independent claims as will become apparent from the following description.

In an embodiment, the present disclosure describes an electronic system for a drug delivery device, the electronic system comprising:

a dose setting and drive mechanism which is configured to perform a dose setting operation for setting a dose to be delivered by the drug delivery device and a dose delivery operation for delivering the set dose, the dose setting and drive mechanism comprising a first member which is a dial sleeve, e.g. a number sleeve, or a member axially and/or rotationally locked thereto and a second member which is a dose and/or injection button or a member axially and/or rotationally locked thereto, wherein the dose setting and drive mechanism is configured such that, at least in the dose delivery operation and/or in the dose setting operation, the first member moves relative to the second member, a communication unit for communicating with another device, an electronic control unit configured to control an operation of the electronic system, the electronic system having a first state in which the communication unit is not activated and a second state in which the communication unit is activated, an electrical use detection unit, the electrical use detection unit being operatively connected to the electronic control unit, the electrical use detection unit being configured to generate a first signal which is indicative that the user has commenced or finished the relative movement between the first member and the second member, wherein the electrical use detection unit comprises at least one electrically conductive spring arm deflectable in response to the relative movement between the first member and the second member to establish or break an electrical connection with at least one electrical contact.

This electronic system may be characterized in that the electronic system comprises a linearly guided switching feature operatively coupled to the first member and/or the second member such that a predefined axial displacement of the first member relative to the second member along a rotation axis of the dose setting and drive mechanism is converted into a radial movement transversely to the rotation axis of the dose setting and drive mechanism, wherein the electronic system is configured such that it is switched from the first state into the second state by the electronic control unit in response to the first signal, thereby inducing the communication unit to establish said communication with another device.

One aspect of the disclosure relates to an electronic system for a drug delivery device. Another aspect of the disclosure relates to a drug delivery device comprising the electronic system. Accordingly, the features described herein with relation to the drug delivery device should be considered as being disclosed for the electronic system and vice versa.

According to one aspect of the present disclosure an electronic system comprises a dose setting and drive mechanism, an electrical power supply, e.g. a rechargeable or non-rechargeable battery, a communication unit for communicating with another device, an electronic control unit and an electrical use detection unit.

In one embodiment, the dose setting and drive mechanism may be configured to perform a dose setting operation for setting a dose to be delivered by the drug delivery device and a dose delivery operation for delivering the set dose. For example, the dose setting and drive mechanism may comprise a first member and a second member and is configured such that, at least in the dose delivery operation and/or in the dose setting operation, the first member moves relative to the second member. Further, the first member may move relative to the second member if a user actuates the device for initiating an operation of the electronic system without performing a dose delivery operation and/or a dose setting operation, e.g. with the dose setting and drive mechanism being in a home position or state. Such a home position or state may be a state after dose delivery and/or prior to setting a new dose. In other words, a user may move the first member relative to the second member, preferably axially, to initiate only an operation of the electronic system, e.g. to initiate a manual syncronisation and/or a pairing with another device or to initiate a mode for amending the settings of the electronic system. Amending the setting of the system may include setting or amending an audible and/or visible feedback or amending display settings. However, such an operation of the electronic system, e.g. to initiate a manual syncronsation and/or a pairing with another device or to initiate a mode for amending the settings of the electronic system, may also occur during a dose delivery operation and/or a dose setting operation, preferably at the end of the dose delivery operation.

In one embodiment, the device or the electronic system comprises an electronic control unit, e.g. comprising a microprocessor or microcontroller. The electronic control unit may be configured to control operation of the drug delivery device or the electronic system. The electronic control unit may be arranged on a conductor carrier and electrically conductively connected with conductors on the conductor carrier. The conductor carrier may be a circuit board such as a printed circuit board. The conductor carrier may be retained in the interior of the user interface member of the system or the device.

The power supply may be arranged in the interior of the electronic system such as in the interior of the user interface member.

In one embodiment, the electronic system has a first state and a second state. The first state and the second state may be different states of operation of the electronic system. In the first state, the system may be in an idle state, where the system could not operate with the desired functionality assigned to the electronic system, e.g. syncronisation or pairing. In other words, the communication unit may be not activated this first state. In the second state, the system may be ready to operate with the desired functionality, e.g. when the system is triggered to start an operation and/or when in the second state a dose setting operation and/or a dose delivery operation is being performed. The electronic system may have an increased electrical power consumption in the second state as compared to the first state. For example, in the second state, one or more electrical or electronic units of the electronic system may be switched to a state of higher power consumption, e.g. an on state, as compared to the first state, where the respective unit may be in a sleep state with low power consumption or an off state with no power consumption at all, e.g. because the connection to an electrical power supply is interrupted. For example, the communication unit may be activated in this second state.

Further, in one embodiment the electrical use detection unit is operatively connected to the electronic control unit and configured to generate a first signal which is indicative that the user has commenced or finished the relative movement between the first member and the second member. The electrical use detection unit may be configured to generate the first signal in response to the relative movement, e.g. in response to a relative axial movement, between the first member and the second member.

The use detection unit may be operatively connected to the electronic control unit, e.g. electrically conductively, such as via a conductor on the conductor carrier. The electrical use detection unit may be configured to generate or trigger a first signal, e.g. an electrical signal. The first signal may be indicative that the user has commenced or finished the relative movement between the first member and the second member, preferably a relative axial movement. Especially, the first signal may be indicative that, with the drug delivery device being in a home position or state, the user has pushed a button or trigger to start or to initiate a manual syncronisation and/or a pairing of the electronic system with another device or to initiate a mode for amending the settings of the electronic system. In addition or as an alternative, the first signal may be indicative that the user has commenced or finished the dose setting operation or the dose delivery operation. Commencement and/or finishing of the dose setting operation or the dose delivery operation may require relative movement between the first member and the second member, e.g. relative axial and/or rotational movement. Accordingly, the first signal may be generated only after the dose delivery operation has been finished or completed. In this way, it can be ensured that an operation requiring energy consumption, like syncronisation or pairing with another device, is only performed if required, namely either if a user manually initiates this operation or if this operation is required after other data has been collected and should be transmitted, e.g. after the dose delivery operation.

Preferably, the electronic system is configured such that it is switched from the first state into the second state by the electronic control unit in response to the first signal, thereby inducing the communication unit to establish said communication with another device, e.g. a syncronisation or pairing operation. In one embodiment, the electronic system is configured such that the electronic system is switched from the first state into the second state by the electronic control unit in response to the first signal. Accordingly, generation of the first signal may be responsible and causal for switching the electronic system to the second state of increased power consumption.

The electronic control unit may, in response to reception of the first signal issue a command, e.g. a signal, to another unit of the electronic system such that this unit is switched on or rendered operational. This unit may be the communication unit for communicating with another device, e.g. a wireless communications interface for communicating with another device via a wireless network such as Wi-Fi or Bluetooth®, or even an interface for a wired communications link, such as a socket for receiving a Universal Series Bus (USB), mini-USB or micro-USB connector. Preferably, the electronic system comprises an RF, WiFi and/or Bluetooth unit as the communication unit. The communication unit may be provided as a communication interface between the system or the drug delivery device and the exterior, such as other electronic devices, e.g. mobile phones, personal computers, laptops and so on. For example, dose data may be transmitted by the communication unit to the external device. The dose data may be used for a dose log or dose history established in the external device.

In one embodiment, the communication unit comprises a wireless communication interface for communicating with another device, wherein the electronic system is configured such that it is switched from the first state into the second state by the electronic control unit in response to the first signal, thereby inducing the communication unit to initiate a manual syncronisation and/or a pairing with another device or to initiate a mode for amending the settings of the electronic system.

There are several different ways suitable to implement the electrical use detection unit. For example, the movement between the first and second member may be detected by means of one or more optical sensor(s), e.g. a radiation detector comprising an electromagnetic radiation emitter, e.g. an LED, and a radiation detector, and/or an acoustic sensor(s), e.g. detecting a click caused by the movement, and/or photoelectric sensor(s), and/or inductive sensor(s), and/or capacitive sensor(s), and/or contact sensor(s), and/or contactless sensor(s), and/or magnetic sensor(s). The electrical use detection unit may comprise at least one sensor, preferably a plurality of sensors.

In one embodiment, the electrical use detection unit comprises at least one electric switch as a sensor. For example, the electrical use detection unit may comprise at least one electrically conductive spring arm deflectable in response to the relative movement, e.g. in response to a relative axial movement, between the first member and the second member to establish or break an electrical connection with at least one electrical contact. The electrical use detection unit may be configured to generate the first signal in response to establishing or breaking the electrical connection between the at least one electrically conductive spring arm and the at least one electrical contact.

In one embodiment, the first member is a dial sleeve, e.g. a number sleeve, or a member axially and/or rotationally locked thereto which first member is rotatable relative to a housing of the dose setting and drive mechanism, e.g. along a helical path, at least in the dose setting operation. In addition, the second member may be a dose and/or injection button or a member axially and/or rotationally locked thereto which second member is axially displaceable relative to the first member and rotationally constrained to the housing at least in the dose delivery operation.

In one embodiment, the first member comprises an encoder ring. The encoder ring may be, permanently or releasably, clipped on a dial sleeve. It may be a unitary component with the dial sleeve. The encoder ring may have a first portion with a first inner diameter and a second portion with a second inner diameter different from the first inner diameter, wherein the first portion and the second portion are located at axially different positions of the encoder ring. Movement of the first member relative to the second member may cause a switching feature which abuts the encoder ring to establish or break an electrical connection, e.g. between the at least one electrically conductive spring arm and the at least one electrical contact, as the switching feature passes from the first portion to the second portion or vice versa. For example, a transition ramp may be provided axially interposed between the first portion and the second portion to facilitate smooth actuation of the switching feature. In addition or as an alternative, the switching feature may be provided with a ramp to facilitate smooth actuation when the switching feature passes from the first portion to the second portion or vice versa.

At least one of the first portion and the second portion may have a smooth cylindrical surface. In addition or as an alternative, one of the first portion and the second portion may be provided with radially inwardly directed ratchet teeth and/or ratchet pockets. Interaction between the switching feature and the ratchet teeth and/or ratchet pockets may occur upon further movement, e.g. a relative rotation, of the first and second member with respect to each other during the dose setting operation or the dose delivery operation. Preferably, one portion is provided with a cylindrical surface, whereas the other portion is provided with ratchet teeth and/or ratchet pockets.

In one embodiment, the ratchet teeth of the ratchet and/or the ratchet pockets may be axially or radially oriented. That is to say, a free end of the teeth may point into the radial direction. The ratchet may be a separate member from the first and second members, e.g. an encoder ring. Alternatively, the ratchet may be one of the first and second members, e.g. the first member. The ratchet may be rotationally locked to one of the first member and the second member. The ratchet may be axially movable relative to the member to which it is connected, e.g. rotationally locked, e.g. in a limited manner. The ratchet may be axially locked to the other one of the first member and the second member, e.g. to the second member.

In a further embodiment, the first member is a dial sleeve, e.g. a number sleeve, or a member axially and/or rotationally locked thereto which first member is axially displaceable relative to a housing of the dose setting and drive mechanism, e.g. along a helical path, at least in the dose delivery operation and wherein the second member is a member, e.g. a pin, axially displaceable relative to the first member upon abutment with the housing or a member axially locked thereto at least in the dose delivery operation. The second member may be guided in a dose and/or injection button or a member axially and/or rotationally locked thereto such that the second member abuts the housing or a member axially locked thereto only if the dose and/or injection button is axially displaced against the bias of a spring. This embodiment is especially applicable if the generation of the first signal is intended when the dose setting and drive mechanism is or approaches the home position or state, i.e. a position or state at the end of or after dose delivery and/or prior to setting a new dose. In more detail, the pin is preferably located in the system such that the pin is moved relative to the dial sleeve when the dial sleeve approaches its home position at the end of dose delivery.

For example, this may be achieved by guiding the pin in a component part moving axially together with the dial sleeve during dose setting and dose delivery. Such a component part may be a clutch sleeve for rotationally coupling the dial sleeve to a driver. Limited relative axial movement between this component part and the dial sleeve may be permitted, e.g. for coupling and/or de-coupling a clutch interface between these two component parts. Preferably, the dial sleeve and the component part, e.g. a clutch sleeve, approach an axial end face of a housing component at the end of dose delivery. The pin may protrude in a first state to abut this end face prior to abutment of the dial sleeve or the clutch sleeve. This causes a relative axial movement between the pin and the dial sleeve.

Still further, an embodiment may comprise the first member being a dose and/or injection button or a top cap thereof and the second member being a chassis or skirt of a dosage knob. In other words, a user interface unit, like a dose and/or injection button and a dosage knob, may comprise two elements at least partially movable relative to each other such that this relative movement may be detected to generate the first signal. For example, the top cap may be axially displaceable and/or axially elastically deformable relative to the second member. Preferably, the electrical use detection unit comprises an axial switch, e.g. mounted on a PCB, such that axial displacement of at least a portion of the top cap relative to the second member actuates the axial switch. Again, this embodiment is applicable if the generation of the first signal is intended when the dose setting and drive mechanism is in the home position or state, i.e. a position or state at the end of or after dose delivery and/or prior to setting a new dose. In addition or as an alternative, the force required to actuate the axial switch may be selected such that the first signal is generated prior to dose delivery, i.e. the force for actuation of the axial switch is lower than the force to be applied for dose delivery.

In an embodiment, the electronic system may be suitable to collect or measure dose data, e.g. corresponding to the set dose or the dispensed dose. Such dose data may be collected only in a third state of the system. According to a further aspect of the present disclosure, the electrical use detection unit may be configured to generate a second use signal which is indicative that the user has commenced the dose setting operation or the dose delivery operation. For example, the electronic system may be configured such that it is switched from the first state or the second state into a third state by the electronic control unit in response to the second use signal. Here, the electrical use detection unit may be configured to generate the second use signal in response to a relative movement of two members of the dose setting and drive mechanism, e.g. in response to a relative rotational movement between a third member of the dose setting and drive mechanism and one of the first member and the second member during the dose delivery operation. In one embodiment, the electrical use detection unit and/or the motion sensing unit, when it is active in the third state of the system, may be operable to gather motion data or measurement data relating to the relative movement the third member and one of the first member and the second member or the relative movement of the first and second members. The electronic control unit may be configured to convert this data into dose data, e.g. characteristic for the size of the dose which has been set or has been delivered in the respective operation.

For example, the second use signal may be indicative that the user has commenced the dose setting operation or the dose delivery operation. Commencement of the dose setting operation or the dose delivery operation may require relative movement between the first member and the second member, e.g. relative rotational movement. Accordingly, the second use signal may be generated only after the dose setting operation or the dose delivery operation has been commenced or initiated. In one embodiment, the use detection unit is configured to generate the second use signal in response to the relative movement, e.g. relative rotational movement, between the first member and the second member, expediently during the dose delivery operation. Thus, the relative movement may be required between the first and the second member for generating the second use signal. This implies that the dose setting or dose delivery operation is actually being performed and, consequently, it is very likely that the system is operated intentionally. This is even more true when the second use signal is generated only during the dose delivery operation, e.g. when the delivery operation has commenced.

In one embodiment, the electronic system may comprise a movable switching feature. Preferably, the switching feature is linearly guided. For example, the switching feature may be received in a guide slot. The switching feature may move only linearly, e.g. radially or axially, as it is linearly guided. This provides a comparatively simple movement type when triggering the use signal. The guide slot may be provided in the second member, for example.

The switching feature may be operatively coupled to one or both of the first member and the second member such that axial displacement of the first member relative to the second member causes movement of the switching feature relative to the first member and/or the second member. The electronic system is preferably configured such that, e.g. axial, movement of the switching feature is used to trigger generation of the first signal. In addition, movement of the same switching feature may be used to trigger generation of the second use signal.

For example, the movable switching feature may be operatively coupled to the first member and/or the second member such that a predefined axial displacement of the first member relative to the second member is converted into movement of the switching feature, e.g. converted into a movement perpendicular to the predefined axial displacement of the first member relative to the second member, to cause generation of the first signal, in particular when the dose setting or dose delivery operation is finished. An additional movement, e.g. a rotation, of the first member relative to the second member may be converted into movement of the switching feature to cause generation of the second use signal.

In one embodiment, the movable switching feature may be resiliently biased into engagement with a block feature before the first member is moved axially a predefined distance relative to the second member. When the first member is moved relative to the second member, the block feature may be removed from the switching feature such that the biasing force can drive the movement of the switching feature to cause generation of the first signal.

In one embodiment, the electronic system comprises a use signal generation interface, for example comprising a ratchet interface such as a radial ratchet interface or an axial ratchet interface. The use signal generation interface may be configured to generate one or more second use signals in response to relative rotation between the first member and the second member. The use signal generation interface may be configured to generate one, e.g. only one, or more second use signals during the dose delivery operation. In case more than one use signal is generated, preferably the first signal which is generated is the one which is used to trigger switching of electronic system from the first state into the second state. The use signal generation interface may be an incremented interface. The use signal generation increment may be an angle. The use signal generation increment may be adjusted to the unit setting increment. Preferably the use signal generation increment is equal to or smaller than the unit setting increment. That is to say, the pitch of the use signal generation increments and the unit setting increments may be equal or the use signal generation increments may be finer pitched. With a finer pitch, a rotation by one unit setting increment may cover more than one use signal generation increments.

In one embodiment, the electronic system or the drug delivery device comprises a movable switching feature. The switching feature may be movable along the rotation axis or the main longitudinal axis of the housing and/or transversely or radially to the rotation axis or the main longitudinal axis of the housing. The switching feature may be rotationally locked to one of the second member and the first member, preferably to the second member. The switching feature may be arranged to move either only radially or only axially or radially and axially. The switching feature may be rigid or, preferably elastically, deformable. The switching feature may be operatively coupled to one of the first member and the second member, e.g. via the use signal generation interface member. For example, the switching feature may engage the ratchet, e.g. the one which defines the second use signal generation increment. The switching feature may be operatively coupled to the first member and/or the second member such that rotation of the first member relative to the second member causes movement of the switching feature relative to the first member, relative to the second member and/or relative to the housing. In addition or as an alternative, the switching feature may be operatively coupled to the first member and/or the second member such that axial displacement of the first member relative to the second member causes movement of the switching feature relative to the first member, relative to the second member and/or relative to the housing. For example, rotation and/or axial displacement of the first member relative to the second member, relative to the switching feature and/or relative to the housing may be converted into movement of the switching feature, e.g. by an operative coupling between the switching feature and a ratchet. Alternatively, rotation and/or axial displacement of the first member relative to the switching feature may remove a mechanical block which blocks movement of the switching feature in a direction into which the switching feature is biased. The movement of the switching feature may be used to trigger generation of the first and/or second use signal. In other words, movement of the switching feature in response to the movement of the first member relative to the second member may be required to generate the first and/or second use signal. For example, to generate or trigger a use signal movement the switching feature may be used to and/or cause a change in the state of an electrical connection, e.g. from open to closed or vice versa, and/or to trigger an electrical switch. The switching feature may be electrically insulating, e.g. of plastic, or it may be electrically conductive, e.g. of metal. If the switching feature is electrically conductive, it may form part of an electrical switch, e.g. of a contact feature of the switch, which is brought into electrical contact with another contact feature of the switch in order to generate the use signal.

In one embodiment, the switching feature engages a ratchet, e.g. a ratchet which may be associated with the first or second member. The switching feature may be biased into engagement with the ratchet, e.g. when it has been displaced out of a ratchet pocket defined between two adjacent ratchet teeth of the ratchet. A biasing force acting on the switching feature may act counter to the direction of movement of the switching feature which causes generation of the first and/or second use signal. For generating a use signal, the switching feature may be moved radially inwardly, for example. In an initial state, e.g. before the dose setting operation or the dose delivery operation is commenced, the switching feature may be engaged with the ratchet pocket defined by adjacent ratchet teeth.

In one embodiment, before the first member is moved relative to the second member and/or before the dose setting operation or the dose delivery operation is commenced, the switching feature is, preferably resiliently, biased into engagement with a block feature with a biasing force. The block feature may block movement of the switching feature relative to the housing in the direction of the biasing force, the first member and/or the second member. The biasing force may be provided by an electrical contact feature, e.g. of a switch, which is resiliently displaced before the dose setting operation and/or the dose delivery operation is commenced. The block feature may be provided by a ratchet tooth between two adjacent ratchet pockets. As an alternative, the block feature may be provided by a transition, e.g. a ramp or a step, between two axially distinct portions of the first member. For example, an encoder ring of the first member has a first portion with a first inner diameter and a second portion with a second inner diameter different from the first inner diameter with the transition between these portions forming the block feature. The biasing force may act in the direction of movement which causes generation of the first and/or second use signal. For example, the switching feature in cooperation with the block feature may maintain a switch in an open condition. When the block feature is removed from the switching feature, the bias may release and the switch may be closed. In order to generate the first and/or second use signal the switching feature may move in the radially outward or radially inward direction, for example.

In one embodiment, the electronic system or the drug delivery device is configured such that movement of the switching feature is used to trigger an electrical switch, e.g. by contacting and/or moving a trigger feature of the switch. When the switch is triggered, the first and/or second use signal may be generated. In response to the use signal, the electronic control unit may switch the electronic system into a different state, e.g. into the second state or into the third state.

The present disclosure is applicable for devices which are manually driven, e.g. by a user applying a force to an injection button, for devices which are driven by a spring or the like and for devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

The present disclosure further pertains to a drug delivery device comprising the electronic system as described above. The drug delivery device may comprise a cartridge containing a medicament.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term “antibody”, as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms “fragment” or “antibody fragment” refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms “Complementarity-determining region” or “CDR” refer to short polypeptide sequences within the variable region of both heavy and light chain polypeptides that are primarily responsible for mediating specific antigen recognition. The term “framework region” refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The terms “axial”, “radial”, or “circumferential” as used herein may be used with respect to a main longitudinal axis of the device, the cartridge, the housing or the cartridge holder, e.g. the axis which extends through the proximal and distal ends of the cartridge, the cartridge holder or the drug delivery device.

BRIEF DESCRIPTION OF THE FIGURES

Non-limiting, exemplary embodiments of the disclosure will now be described with reference to the accompanying drawings, in which.

In the figures, identical elements, identically acting elements or elements of the same kind may be provided with the same reference numerals.

DETAILED DESCRIPTION

Figure 1:
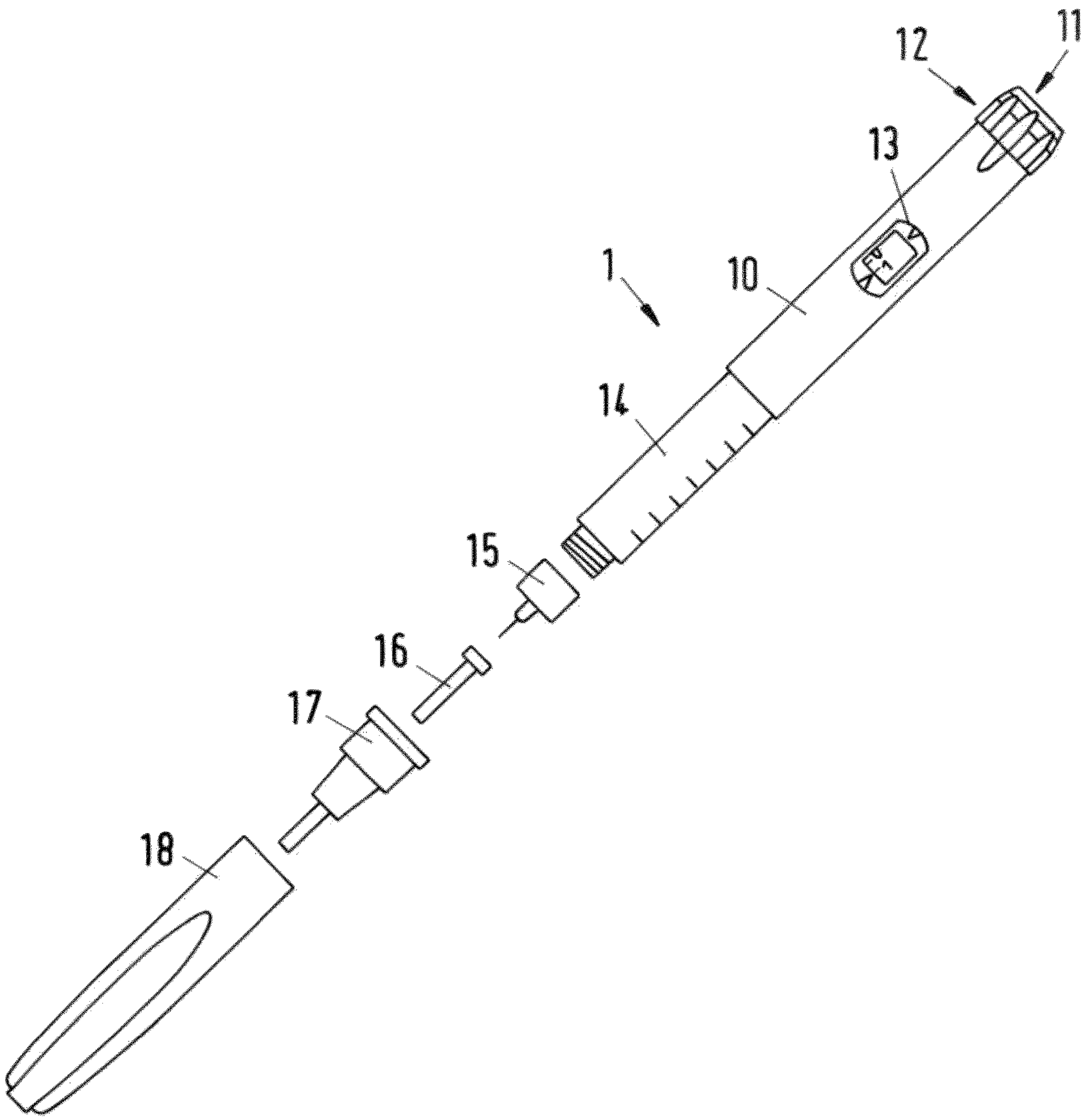
FIG. 1 shows an embodiment of a drug delivery device.

In the following, some embodiments will be described with reference to an insulin injection device. The present disclosure is however not limited to such application and may equally well be deployed with injection devices that are configured to eject other medicaments or drug delivery devices in general, preferably pen-type devices and/or injection devices.

Embodiments are provided in relation to injection devices, in particular to variable dose injection devices, which record and/or track data on doses delivered thereby. These data may include the size of the selected dose and/or the size of the actually delivered dose, the time and date of administration, the duration of the administration and the like. Features described herein include the arrangement of sensing elements and power management techniques (e.g. to facilitate small batteries and/or to enable efficient power usage).

Certain embodiments in this document are illustrated with respect to Sanofi's AMSTAR® injection device where an injection button and grip (dose setting member or dose setter) are combined. The injection button may provide the user interface member for initiating and/or performing a dose delivery operation of the drug delivery device. The grip or knob may provide the user interface member for initiating and/or performing a dose setting operation. Both devices are of the dial extension type, i.e. their length increases during dose setting. Other injection devices with the same kinematical behaviour of the dial extension and button during dose setting and dose expelling operational mode are known as, for example, the Kwikpen® device marketed by Eli Lilly and the Novopen® 4 device marketed by Novo Nordisk. An application of the general principles to these devices therefore appears straightforward and further explanations will be omitted. However, the general principles of the present disclosure are not limited to that kinematical behaviour. Certain other embodiments may be conceived for application to Sanofi's SoloSTAR® injection device where there are separate injection button and grip components/dose setting members. Thus, there may be two separate user interface members, one for the dose setting operation and one for the dose delivery operation.

"Distal" is used herein to specify directions, ends or surfaces which are arranged or are to be arranged to face or point towards a dispensing end of the drug delivery device or components thereof and/or point away from, are to be arranged to face away from or face away from the proximal end. On the other hand, "proximal" is used to specify directions, ends or surfaces which are arranged or are to be arranged to face away from or point away from the dispensing end and/or from the distal end of the drug delivery device or components thereof. The distal end may be the end closest to the dispensing and/or furthest away from the proximal end and the proximal end may be the end furthest away from the dispensing end. A proximal surface may face away from the distal end and/or towards the proximal end. A distal surface may face towards the distal end and/or away from the proximal end. The dispensing end may be the needle end where a needle unit is or is to be mounted to the device, for example.

FIG. 1 is an exploded view of a medicament delivery device or drug delivery device. In this example, the medicament delivery device is an injection device 1, e.g. a pen-type injector, such as Sanofi's AllSTAR® injection pen.

The injection device 1 of FIG. 1 is an injection pen that comprises a housing 10 and contains a container 14, e.g. an insulin container, or a receptacle for such a container. The container may contain a drug. A needle 15 can be affixed to the container or the receptacle. The container may be a cartridge and the receptacle may be a cartridge holder. The needle is protected by an inner needle cap 16 and either an outer needle cap 17 or another cap 18. An insulin dose to be ejected from injection device 1 can be set, programmed, or 'dialed in' by turning a dosage knob 12, and a currently programmed or set dose is then displayed via dosage window 13, for instance in multiples of units. The indicia displayed in the window may be provided on a number sleeve or dial sleeve. For example, where the injection device 1 is configured to administer human insulin, the dosage may be displayed in so-called International Units (IU), wherein one IU is the biological equivalent of about 45.5 micrograms of pure crystalline insulin (1/22 mg). Other units may be employed in injection devices for delivering analogue insulin or other medicaments. It should be noted that the selected dose may equally well be displayed differently than as shown in the dosage window 13 in FIG. 1.

The dosage window 13 may be in the form of an aperture in the housing 10, which permits a user to view a limited portion of a dial sleeve 20 that is configured to move when the dosage knob 12 is turned, to provide a visual indication of a currently set dose. The dosage knob 12 is rotated on a helical path with respect to the housing 10 when setting a dose.

In this example, the dosage knob 12 includes one or more formations to facilitate attachment of a data collection device.

The injection device 1 may be configured so that turning the dosage knob 12 causes a mechanical click sound to provide acoustic feedback to a user. In this embodiment, the dosage knob or dose button 12 also acts as an injection button 11. When needle 15 is stuck into a skin portion of a patient, and then dosage knob 12/injection button 11 is pushed in an axial direction, the insulin dose displayed in display window 13 will be ejected from injection device 1.

When the needle 15 of injection device 1 remains for a certain time in the skin portion after the dosage knob 12 is pushed, the dose is injected into the patient's body. Ejection of the insulin dose may also cause a mechanical click sound, which may be different from the sounds produced when rotating the dosage knob 12 during dialing of the dose.

In this embodiment, during delivery of the insulin dose, the dosage knob 12 is returned to its initial position in an axial movement, without rotation, while the dial sleeve 20 is rotated to return to its initial position, e.g. to display a dose of zero units. As noted already, the disclosure is not restricted to insulin but should encompass all drugs in the drug container 14, especially liquid drugs or drug formulations.

Injection device 1 may be used for several injection processes until either the insulin container 14 is empty or the expiration date of the medicament in the injection device 1 (e.g. 28 days after the first use) is reached. In the case of a resuable device, it is possible to replace the insulin container.

Furthermore, before using injection device 1 for the first time, it may be necessary to perform a so-called "prime shot" to remove air from insulin container 14 and needle 15, for instance by selecting two units of insulin and pressing dosage knob 12 while holding injection device 1 with the needle 15 upwards. For simplicity of presentation, in the following, it will be assumed that the selected amounts substantially correspond to the injected doses, so that, for instance the amount of medicament selected from the injection device 1 is equal to the dose received by the user.

As explained above, the dosage knob 12 also functions as an injection button 11 so that the same component is used for dialling/setting the dose and dispensing/delivering the dose.

Figure 18:
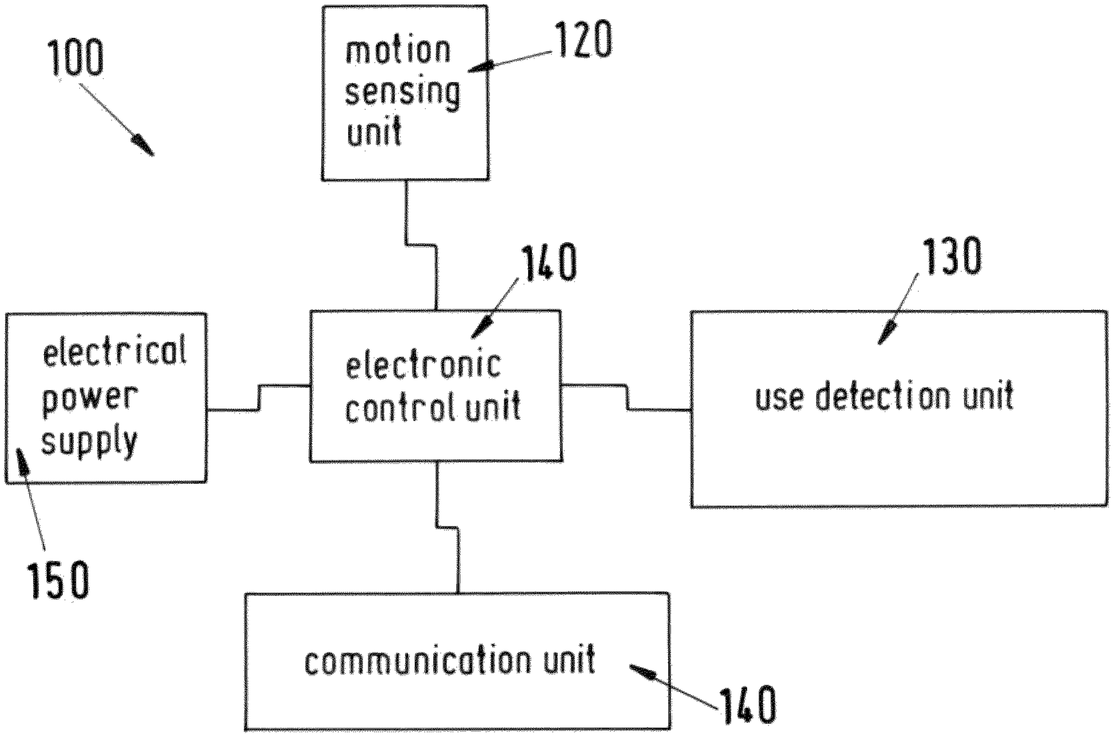
FIG. 18 illustrates schematically an embodiment of an electronic system for a drug delivery device.

In the following, an electronic system 100 according to the disclosure will be described with respect to several different exemplary embodiments. The electronic system 100 comprises a dose setting and drive mechanism which may be part of an injection device 1 as depicted in FIG. 1 and an electrical power supply 150, e.g. a rechargeable or non-rechargeable battery, as shown in FIG. 18. The electronic system further comprises an electronic control unit 110 configured to control an operation of the electronic system which has a first state and a second state, wherein the electronic system has an increased electrical power consumption in the second state as compared to the first state. The electronic system further comprises an electrical use detector unit 130 which is operatively connected to the electronic control unit 110 and which is configured to generate at least a first signal which is indicative that the user performs an operation. An example of such an operation is that the user of the injection device and/or the electronic system enters a manual synchronization or pairing mode of the electronic system. The electronic system is configured such that it is switched from the first state into the second state by the electronic control unit 110 in response to said first signal. The electronic system further comprises a communication unit 140 for communicating with another device. When the communication unit is active to perform the manual synchronization or pairing mode, the electronic system is in its second state.

The present disclosure comprises several alternatives for generating the first signal by means of an electrical use detector unit 130. In more detail, the embodiments are based on detecting an axial movement of a first member of the dose setting and drive mechanism with respect to a second member of the dose setting and drive mechanism.

Figure 2:
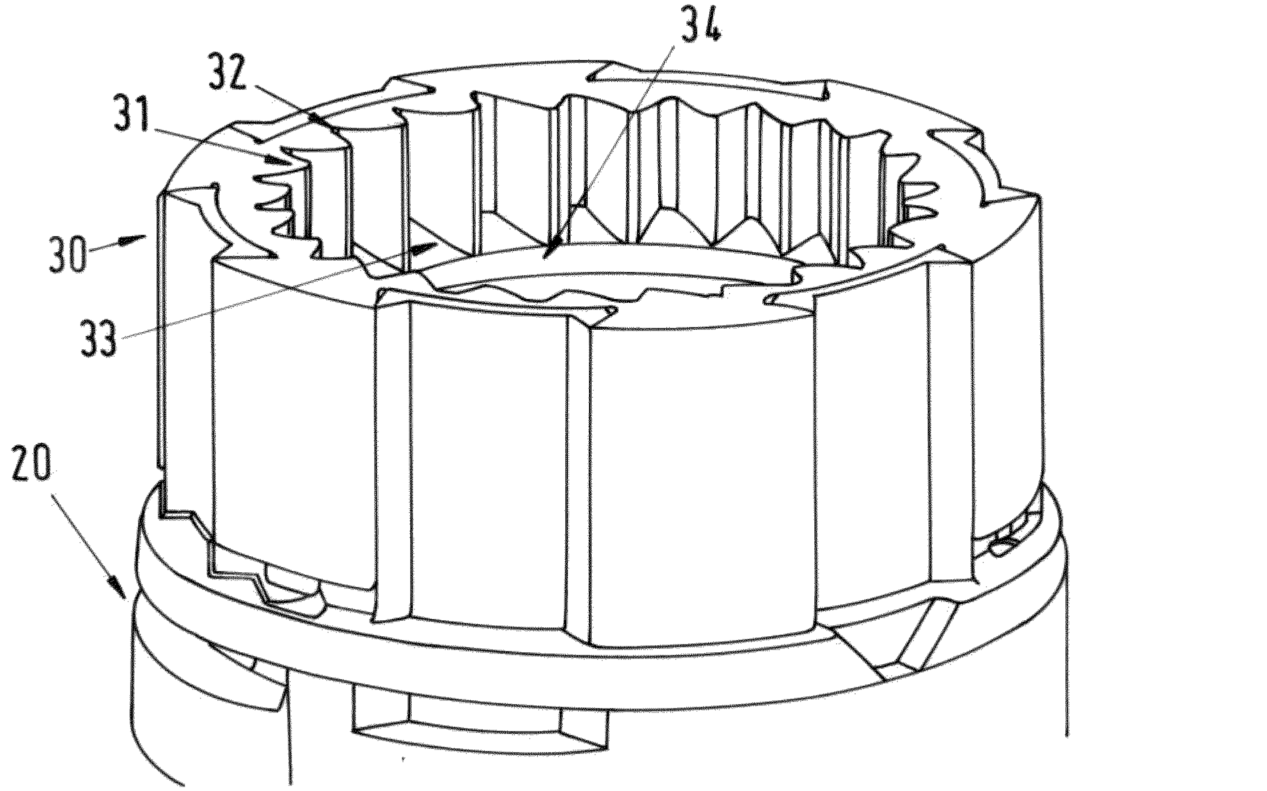
FIG. 2 shows a perspective view of an encoder of a system of a first embodiment.
Figure 3:
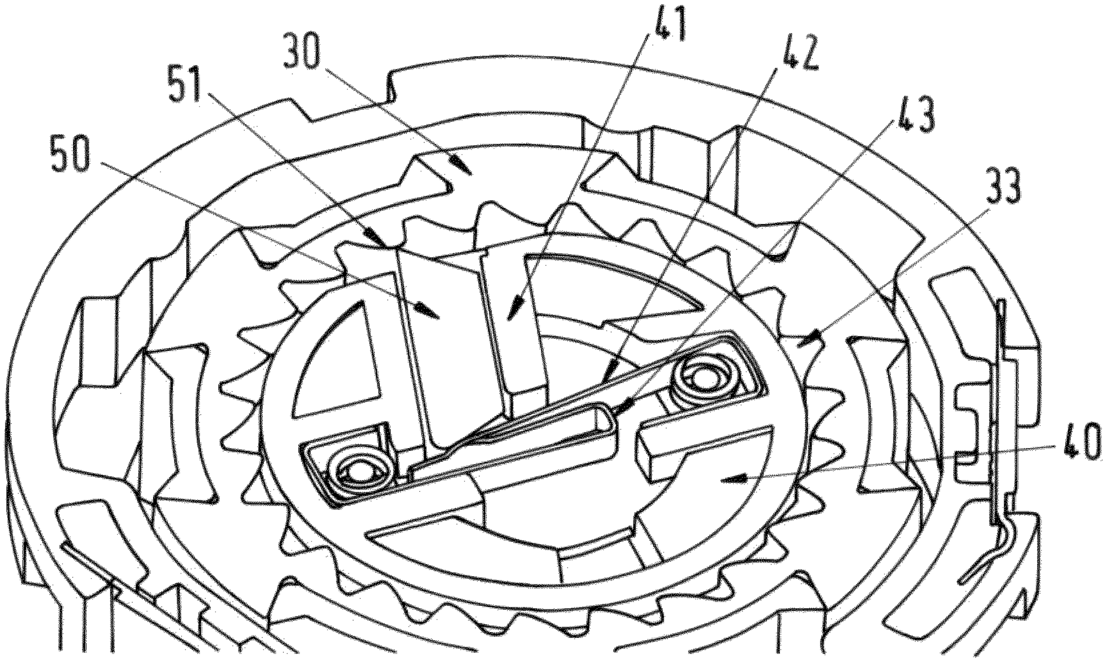
FIG. 3 shows a cut-away view on a portion of the system of the first embodiment.

A first embodiment is depicted in FIGS. 2 to 4. In this embodiment relative axial movement of the button 11 with respect to the dose dial sleeve 20 causes generation of the first signal. FIG. 2 shows the proximal end of the dose dial sleeve 20 which is provided with an encoder ring 30 which may be a unitary component part with the dose dial sleeve 20 or which may be a separate component part rigidly constrained to the dose dial sleeve 20. In other words, the dose dial sleeve 20 and the encoder ring 30 behave as a single component part. As can be seen in FIG. 2, the encoder ring 30 is provided with a series of radially oriented ratchet teeth 31 arranged between ratchet pockets 32. Towards its distal end, the encoder ring 30 is provided with a transition ramp 33 which ends in a cylindrical portion 34 with a continuous cylindrical inner surface. The inner diameter of the cylindrical portion 34 substantially corresponds to the inner diameter of the tips of the ratchet teeth 31. This inner diameter of the cylindrical portion 34 is smaller compared to the inner diameter defined by the ratchet pockets 32.

FIG. 3 shows the encoder ring 30 and the dose dial sleeve 20 in a sectional view through a plane in the transition ramp 33. Further, FIG. 3 shows a chassis 40 arranged within the space defined by the encoder ring 30 and the dose dial sleeve 20. The chassis 40 may be retained in or may be part of button 11 or a driver of the dose setting and drive mechanism.

The chassis 40 has a substantially circular outer shape and is provided with a guiding groove 41 running in a direction perpendicular to the axis of rotation of the dose dial sleeve 20. Further, the chassis 40 is provided with two electrical contacts 42, 43 in the form of metal pressings fixed within the chassis 40. The electrical contacts 42, 43 form a switch which is open in a condition with no forces acting on the electrical contacts 42, 43. The switch may be closed by elastically deflecting the electrical contact 42 towards the electrical contact 43.

A switching feature in the form of a shuttle 50 is guided in the guiding groove 41 of the chassis 40 such that the shuttle 50 is allowed to be axially displaced within the guiding groove 41. A radially outwards facing tip of the shuttle 50 is formed as a ratchet tooth 51 mating with the ratchet teeth 31 and the ratchet pockets 32 of the encoder ring 30. The length of the shuttle 50 is chosen such that the electrical contact 42 biases the shuttle 50 into one of the ratchet pockets 32 depending on the relative rotational position of the chassis 40 with respect to the encoder ring 30. However, upon relative rotation between the encoder ring 30 and the chassis 40, for example during dose delivery, the shuttle 50 is pushed inwards by engagement with the respective ratchet tooth 31 against the bias of the electrical contact 42 which is deflected to close the switch by contacting the electrical contact 43 as shown in FIG. 3.

During a dose setting operation of the injection device 1 the relative axial position of the chassis 40 with respect to the encoder ring 30 is such that the shuttle 50 is aligned with the proximal portion of the encoder ring 30 allowing interaction between the shuttle 50 and the ratchet teeth 31 and the ratchet pockets 32. However, upon actuation of the button 11 the chassis 40 may be axially displaced axially with respect to the encoder ring 30 such that the shuttle 50 is guided along the transition ramp 33 to engage the cylindrical portion 34. This relative axial movement between the chassis 40 and to the encoder ring 30 may occur only at the end of dose delivery. As shown in FIG. 3, the shuttle 50 is pushed radially inwards when engaging the cylindrical portion 34, thereby closing the switch formed by the electrical contacts 42, 43. In contrast to the dose setting or dose delivery operation, when the shuttle 50 oscillates upon rotation of the dose dial sleeve 20 with the encoder ring 30 relative to the chassis 40, thereby repeatedly opening and closing the switch formed by electrical contacts 42, 43, the switch is permanently closed when the shuttle 40 has been moved axially with respect to the encoder ring 30 such that the shuttle 50 engages the cylindrical portion 34. The electrical system 100, more specifically the use detection unit 130, detects the permanent closing of the switch and generates a first signal which may activate a manual synchronization or pairing mode.

As is apparent from FIG. 3, the first signal may not only be generated at the end of dose delivery but may also be generated with the injection device being in the home state or position, i.e. prior to dose setting. In such a home state the button 11 simply has to be pressed to activate a manual synchronization or pairing mode of the electrical system.

The switch formed by electrical contacts 42, 43 may further be part of a motion sensing unit 120 of the electrical system 100 detecting relative rotation between the dose dial sleeve 20 and the chassis 40 during dose delivery as the shuttle 50 is repeatedly closing the second switch formed by the electrical contacts 42 and 43. This condition may generate a second use signal which may turn on encoder functions of the electrical system.

Figure 4A:
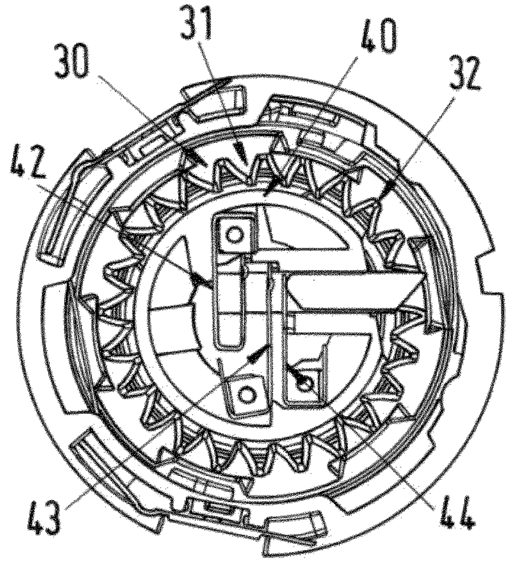
FIGS. 4*a-c* show a cut-away view on a portion of the system of a second embodiment in different states.
Figure 4B:
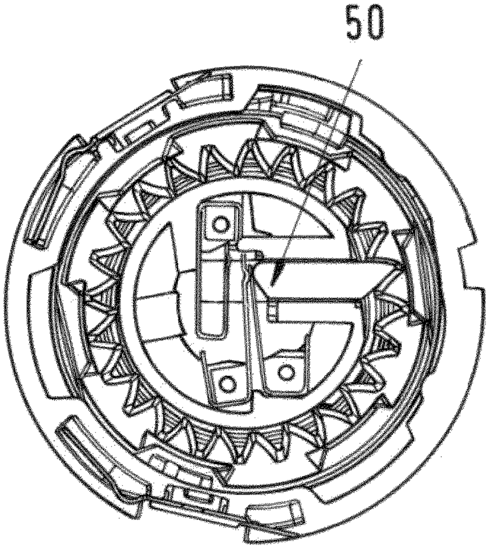
Figure 4C:
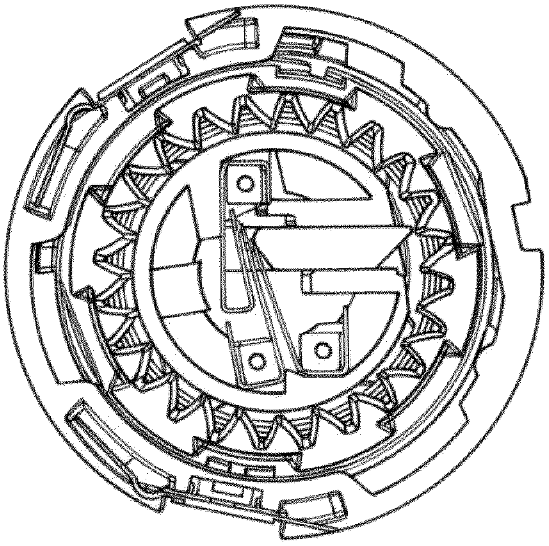
Figure 5:
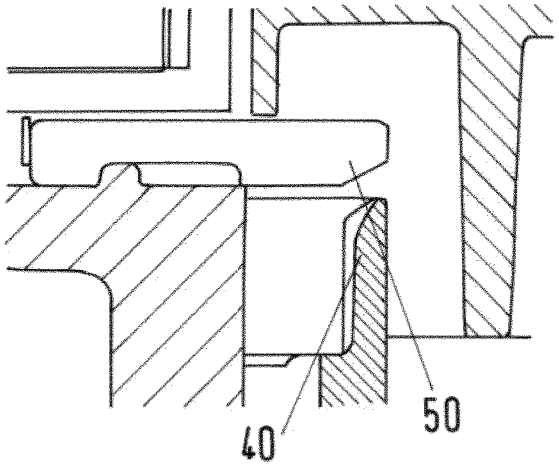
FIG. 5 shows a sectional view on a portion of the system of the second embodiment.

A second embodiment is depicted in FIGS. 4*a* to 5 which is similar to the first embodiment. Again, the dose dial sleeve 20 is provided with an encoder ring 30 having ratchet teeth 31 and ratchet pockets 32. Further, a chassis 40 is provided with a guiding groove 41 guiding shuttle 50, suitable for engaging ratchet teeth 31 and ratchet pockets 32.

In contrast to the first embodiment, the second embodiment comprises two switches formed by electrical contacts 42, 43 and 44. Further, the axial position between the chassis 40 and the encoder ring 30 is such that in the home state or position of the injection device 1, i.e. prior to dose setting, the shuttle 50 is located proximally spaced from the encoder ring 30 as shown in FIG. 5. This position is further depicted in FIG. 4*a* where it is shown that the shuttle 50 is pushed radially outwards by the electrical contact 44. In this condition, i.e. prior to the button 11 being pressed, neither switch is closed as the electrical contacts 42, 43 and 44 are not deflected by the shuttle 50.

FIG. 4*b* shows a condition when the button 11 is pressed, thereby axially displacing the chassis 40 with respect to the encoder ring 30. This results in pushing the shuttle 50 radially inwards to the major diameter of the ratchet, i.e. the diameter defined by the ratchet pockets 32. Due to this displacement of the shuttle 50 the first switch between the electrical contact 44 and the electrical contact 42 is closed. By closing this first switch the first signal is generated, thereby turning on the manual synchronization and pairing function of the electrical system.

FIG. 4*c* shows a condition when the dose dial sleeve 20 with the encoder ring 30 starts to rotate with respect to the chassis 40, for example during dose delivery. Due to this rotation, of the shuttle 50 is repeatedly pushed radially inwards to the minor diameter of the ratchet, i.e. the inner diameter defined by the tips of the ratchet teeth 31, thereby repeatedly closing the second switch formed by the electrical contacts 42 and 43 as described above with respect to the first embodiment. This condition may generate a second use signal which may turn on encoder functions of the electrical system.

Figure 6:
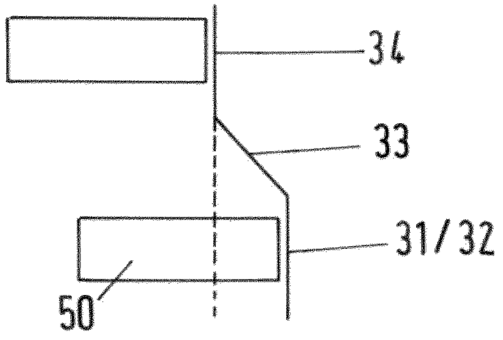
FIG. 6 shows a sketch of the system of a third embodiment.
Figure 7A:
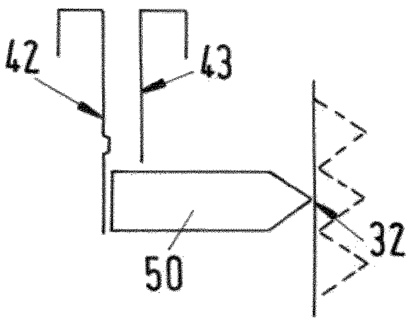
FIGS. 7*a-c* show a portion of the system of a third embodiment in different states.
Figure 7B:
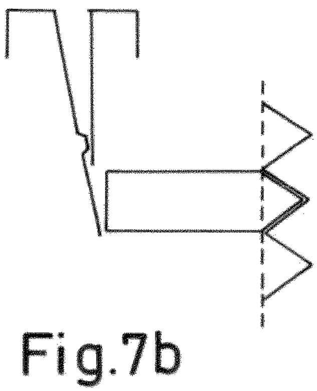
Figure 7C:
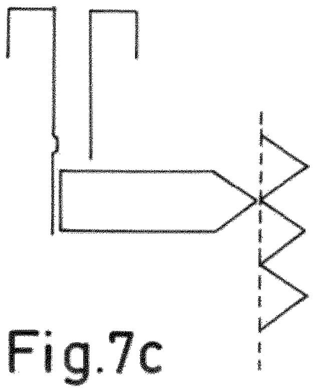
Figure 8:
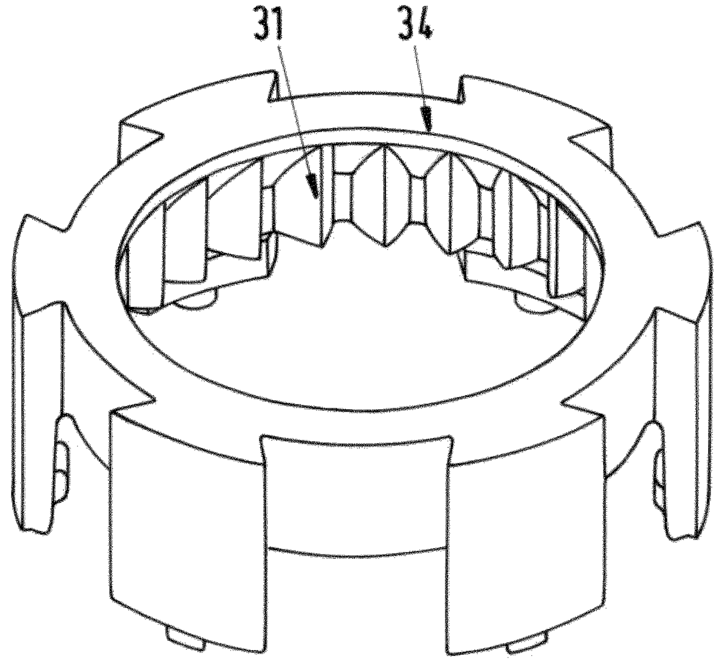
FIG. 8 shows an encoder ring of the third embodiment.

The third embodiment is depicted in FIGS. 6 to 8 which is similar to the first embodiment. Again, the dose dial sleeve 20 (not shown) is provided with an encoder ring 30 having ratchet teeth 31 and ratchet pockets 32. Further, a chassis 40 (not shown) is provided with a guiding groove 41 guiding shuttle 50 suitable for engaging ratchet teeth 31 and ratchet pockets 32.

In contrast to the first embodiment, the third embodiment comprises a cylindrical portion 34 of the encoder ring 30 located at the proximal end of the encoder ring 30. Thus, the ratchet formed by ratchet teeth 31 and ratchet pockets 32 is located distally of the cylindrical portion 34. In addition, the design of the electrical contacts 42, 43 is amended such that the switch formed by the electrical contacts 42, 43 is open when the shuttle 50 abuts the cylindrical portion 34 or is pushed radially inwards by the contact with the ratchet teeth 31. On the other hand, the switch formed by the electrical contacts 42, 43 is closed as the shuttle 50 is allowed to enter into the ratchet pockets 32 due to the bias of the electrical contact 42 acting on the shuttle 50. In other words, the third embodiment operates substantially inverse compared to the first embodiment.

In a similar manner as in the first embodiment, the encoder ring 30 of the third embodiment may be provided with a transition ramp 33 between the cylindrical portion 34 and the ratchet portion 31, 32. In addition or as an alternative, the shuttle 50 may be provided with a respective ramp at the ratchet tooth 51.

In the third embodiment, the shuttle 50 is held on the cylindrical portion 34 of the encoder ring 30 in the home position or state, i.e. prior to dose setting. In this condition the switch 42, 43 is open. The switch 42, 43 remains open during dose setting when the user rotates the dose dial sleeve 20 by means of the dosage knob 12. As soon as the user presses the button 11, i.e. causes a relative axial movement of the button 11 (with chassis 40) with respect to the dose dial sleeve 20 (with encoder ring 30), the shuttle 50 falls into the ratchet pocket 32 biased by the electrical contact 42, thereby closing the switch 42, 43. This closing of the switch is detected and causes generation of the first signal, thereby turning on the manual synchronization and pairing function of the electrical system.

During the dose delivery operation, the shuttle 50 is repeatedly pushed radially inwards against the bias of the electrical contact 42 by interaction of the ratchet tooth 51 with the ratchet teeth 31. Thus, the switch 42, 43 is repeatedly opened and closed (as the ratchet tooth 51 falls back into one of the ratchet pockets 32). This may be detected and may cause generation of a second use signal, thereby turning on an encoder function of the electrical system.

A fourth embodiment is depicted in FIGS. 9*a* to 13. Again, the dose dial sleeve 20 is provided with an encoder ring 30 having ratchet teeth 31 and ratchet pockets 32. Further, a chassis 40 is provided with a guiding groove 41 guiding shuttle 50 suitable for engaging ratchet teeth 31 and ratchet pockets 32. In addition, electrical contacts 42, 43 are provided in a similar configuration as in the first embodiment, i.e. a switch formed by of the contacts 42, 43 is open if the ratchet tooth 51 of the shuttle 50 engages the ratchet pocket 32 and the switch is closed as the ratchet tooth 51 passes over one of the ratchet teeth 31 and is pushed radially inwards against the bias of electrical contact 42.

In contrast to the first to third embodiments, the encoder ring 30 is not provided with a cylindrical portion intended for engagement with the shuttle 50. Thus, the encoder ring 30 may be shorter in the axial direction compared to the first to third embodiments. The dose setting and drive mechanism of the fourth embodiment further comprises a clutch sleeve 60 and an inner housing 70. The clutch sleeve 60 may be provided with a ring of clutch teeth 61 (FIG. 12) provided on a flange-like portion 62 for engagement with a corresponding ring of clutch teeth 21 provided on the dose dial sleeve 20. A clutch spring (not shown) may be provided acting on the clutch sleeve 60 to push the clutch teeth 21 into engagement with the clutch teeth 61. The clutch teeth 21, 61 may be disengaged against the bias of the clutch spring when the user pushes the button 11, e.g. for the dose delivery operation, thereby displacing the clutch sleeve 60 axially with respect to the dose dial sleeve 20. The dose dial sleeve 20 may be in threaded engagement with the inner housing 70 such that the dose dial sleeve 20 is guided along a helical path during dose setting operation and dose delivery operation. Further, the inner housing 70 is provided with a proximal end face 71 for abutment with the flange-like portion 62 of the clutch sleeve 60. The distal side of the flange-like portion 62 abuts the proximal end face 71 at the end of dose delivery when the button 11 is pressed. After a user releases the button 11, the clutch spring lifts the flange-like portion 62 away from the proximal end face 71, thereby re-engaging clutch teeth 21, 61.

Figure 9A:
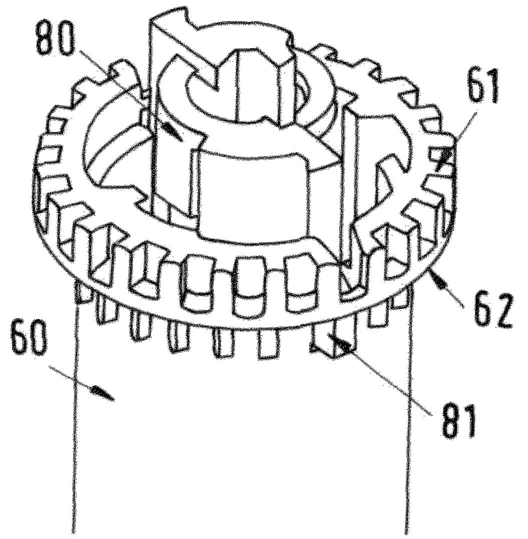
FIGS. 9*a-b* show a cut-away view on a portion of the system of a fourth embodiment in different states.
Figure 9B:
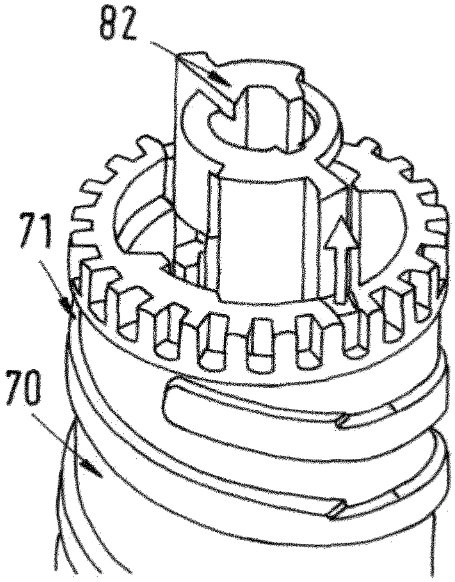
Figure 10A:
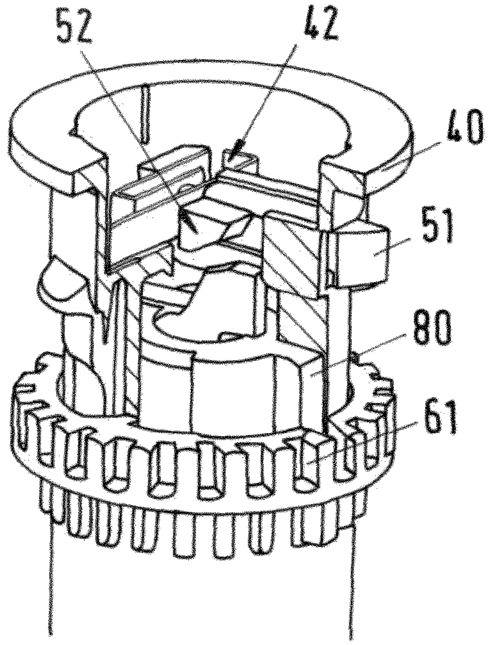
FIGS. 10*a-b* show a cut-away view on a portion of the system of the fourth embodiment in different states.
Figure 10B:
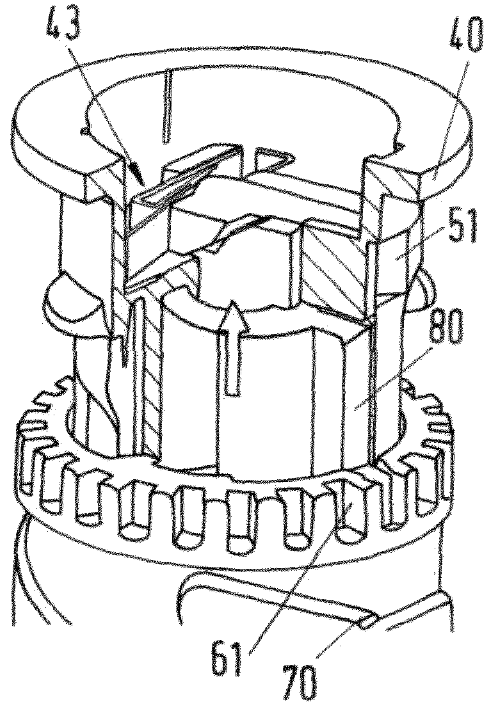
Figure 11:
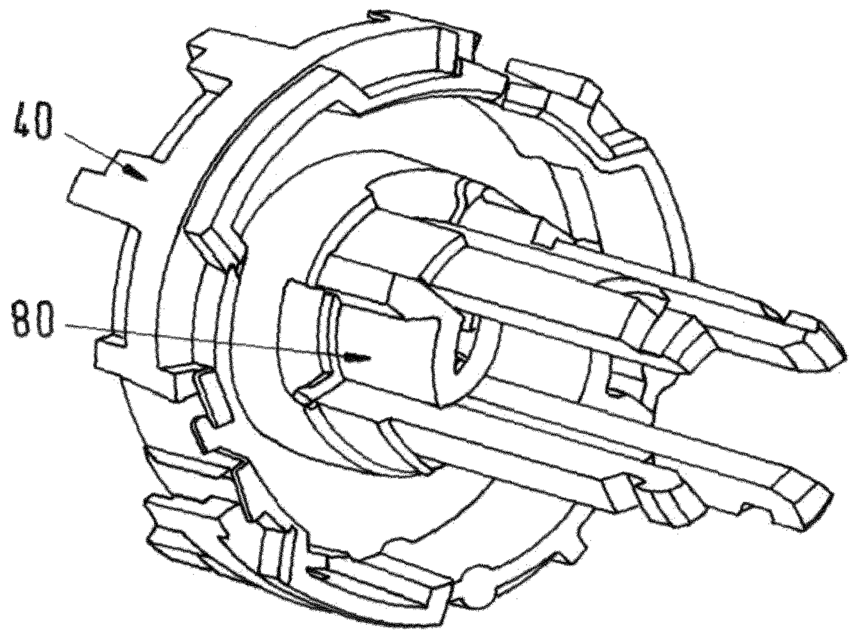
FIG. 11 shows a perspective view of a portion of the system of the fourth embodiment.
Figure 12:
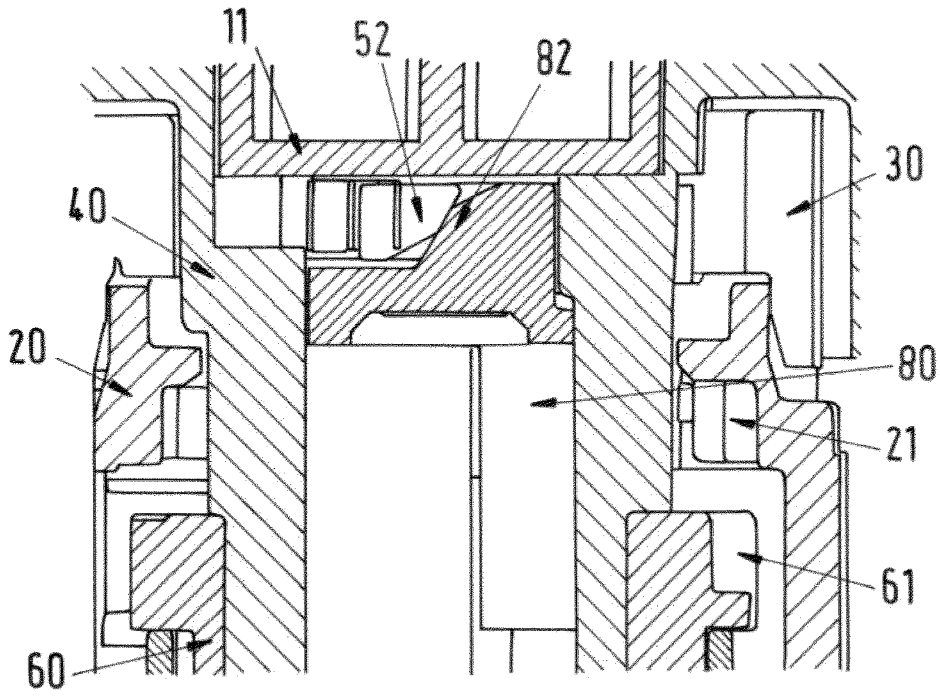
FIG. 12 shows a sectional view on a portion of the system of the fourth embodiment.
Figure 13:
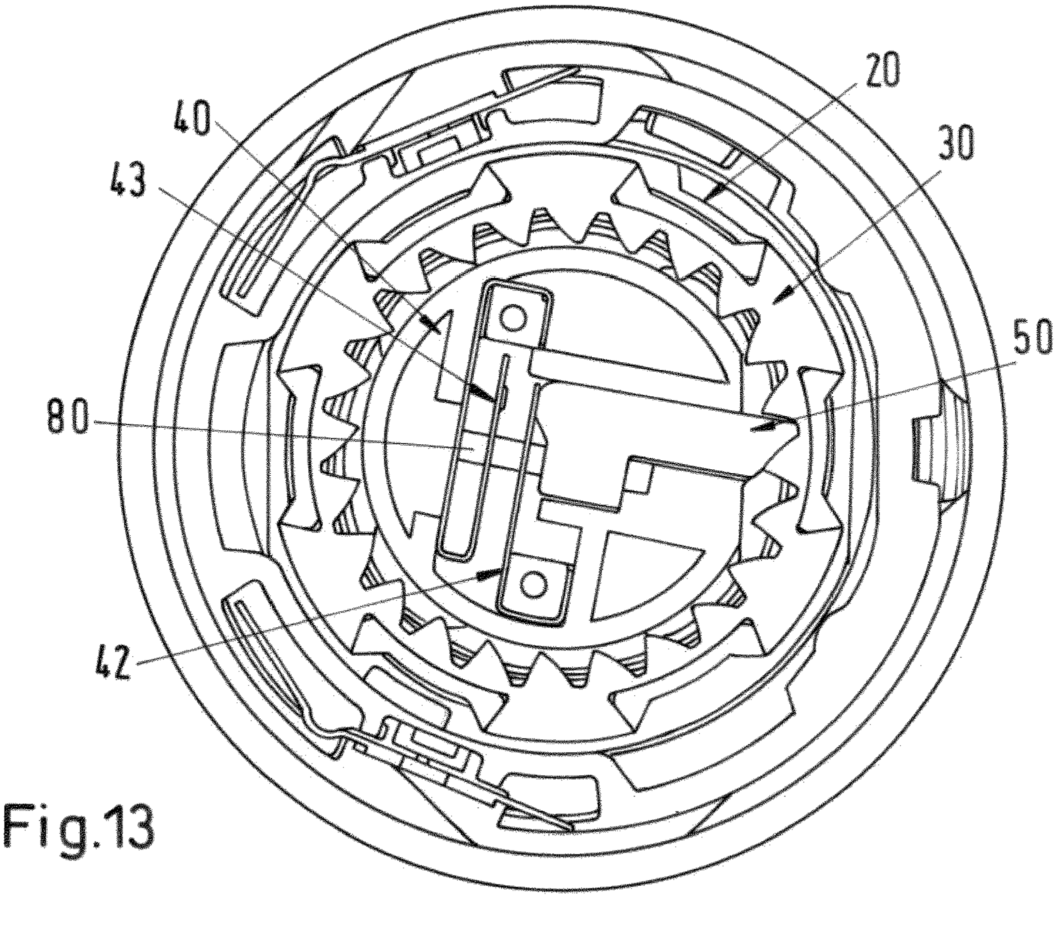
FIG. 13 shows a top view on a portion of the system of the fourth embodiment.
Figure 14:
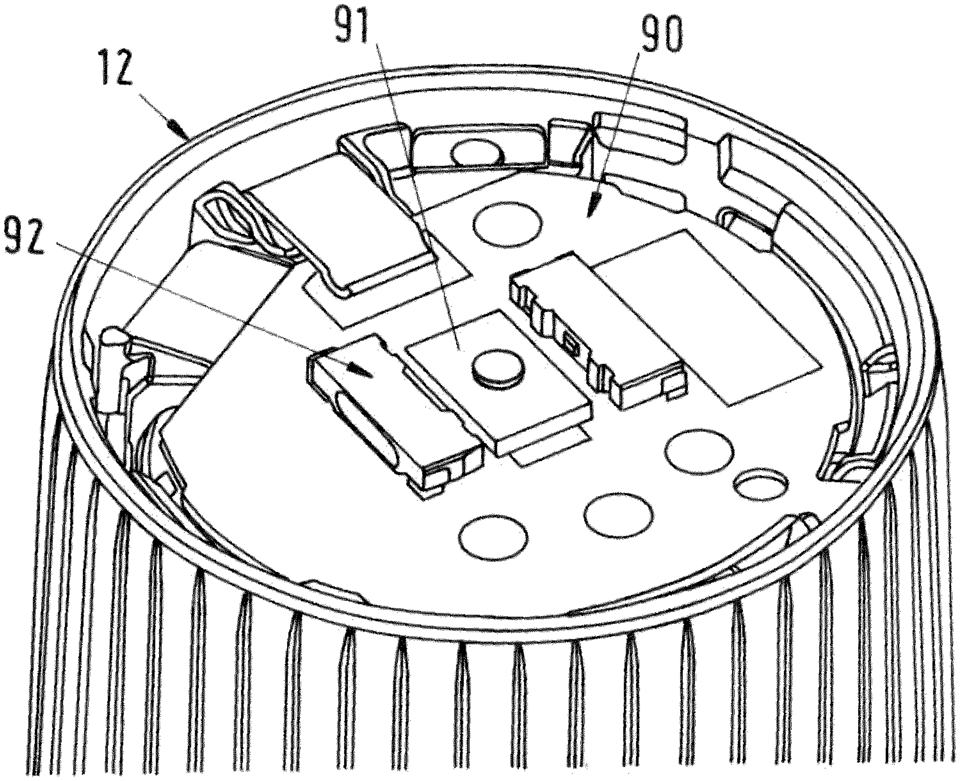
FIG. 14 shows a perspective view of a portion of the system of a fifth embodiment with removed cap.
Figure 15:
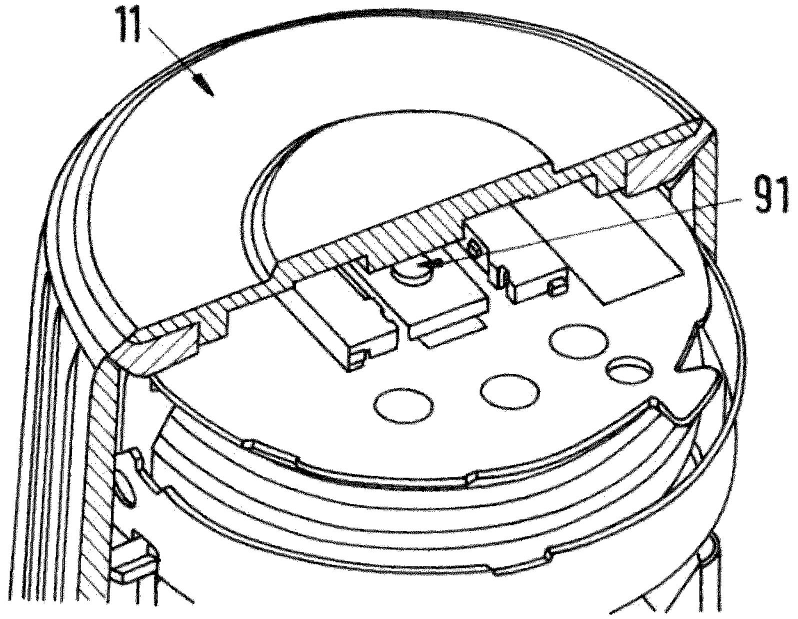
FIG. 15 shows a perspective view of the system of FIG. 14 with a partially cut away cap.

The dose setting and drive mechanism of the fourth embodiment further comprises a pin 80 which is guided in the chassis 40 such that a relative axial movement of the pin 80 relative to the chassis 40 is permitted. The pin 80 comprises a finger 81 which passes through a cut out in the flange-like portion 62 of the clutch sleeve 60 and protrudes distally through the flange-like portion 62 as shown in FIGS. 9*a* and 10*a*. Further, the pin 80 comprises a ramp 82 on the proximal side of the pin 80. This ramp 82 passes through a cut out in the guiding groove 41 of the chassis 44 engagement with a corresponding ramp 52 of the shuttle 50.

As the finger 81 of the pin 80 protrudes distally through the flange-like portion 62, the distal end of finger 81 abuts the proximal end face 71 of the inner housing 70 at the end of dose delivery, i.e. when the dose dial sleeve 20 and the clutch sleeve 60 are moved distally with respect to the inner housing 70. This results in an axial displacement of the pin 80 with respect to the chassis 40 such that the ramp 82 engages the ramp 52 of the shuttle 50 and pushes the shuttle 50 radially inwards against the bias of electrical contact 42, thereby closing the switch formed by electrical contacts 42, 43. By closing this switch the first signal is generated, thereby turning on the manual synchronization and pairing function of the electrical system.

During the dose delivery operation, the shuttle 50 is repeatedly pushed radially inwards against the bias of the electrical contact 42 by interaction of the ratchet tooth 51 with the ratchet teeth 31 as explained above with respect to the first embodiment. Thus, the switch 42, 43 is repeatedly opened and closed (as the ratchet tooth 51 falls back into one of the ratchet pockets 32). This may be detected and may cause generation of a second use signal, thereby turning on an encoder function of the electrical system.

A fifth embodiment is depicted in FIGS. 14 to 17. In this fifth embodiment, the electrical use detection unit 130 for detecting the first signal which causes turning on the manual synchronization and pairing function of the electrical system is located in the dosage knob 12 below the button 11. In contrast to other embodiments in which the dosage knob 12 and the button 11 may be a single unitary component part, the button 11 is formed as a separate cap which is attached to the skirt of the dosage knob 12 during assembly of the system or device. A printed circuit board (PCB) 90 is located within the dosage knob 12 below the button 11 with an axial switch 91 provided, e.g. centrally, on the PCB 90. The PCB 90 may further comprise other electronic components, like LEDs 92.

Figure 16:
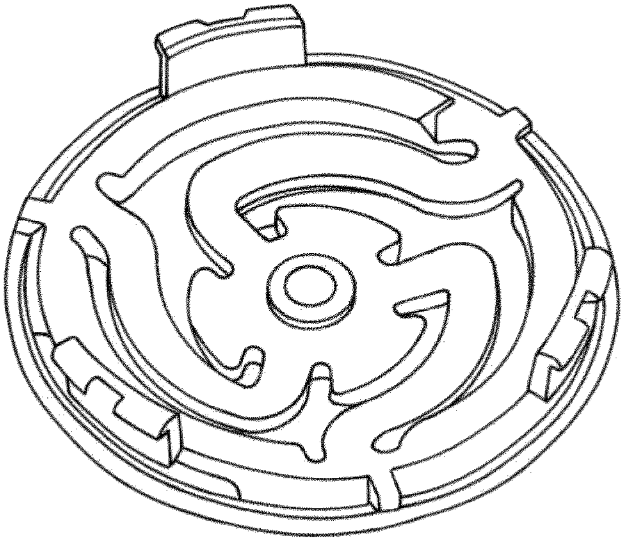
FIG. 16 shows a perspective view of the cap of the system of FIG. 15.
Figure 17:
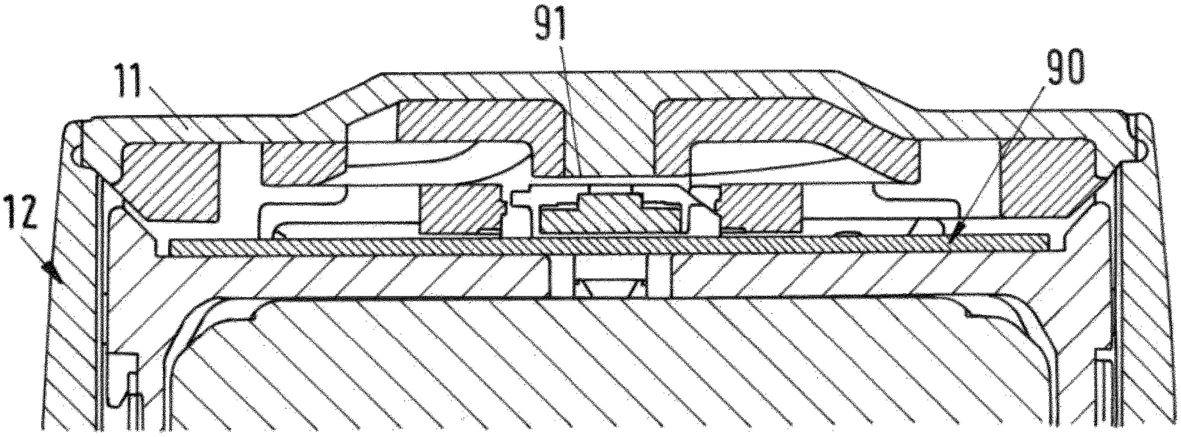
FIG. 17 shows a sectional view of a portion of the system of the fifth embodiment.

In the fifth embodiment, the cap-like button 11 is elastically deformable, for example by means of a skeleton as depicted in FIG. 16. This skeleton is preferably covered by the skin of a softer material such that the skin may form a seal by means of a circumferential bead engaging a respective groove in the skirt of the dosage knob 12 as shown in FIG. 17. The skin may further comprise a translucent portion such that a back-lit logo or the like may be provided on the button 11 which may be indicative of an operation of the electronic system, for example the manual synchronization and pairing function of the electrical system.

The force required for actuation of the axial switch 91 may be selected depending on the intended function. Thus, it is possible to actuate the axial switch 91 by the relatively low force such that the axial switch 91 is activated prior to disengagement of a clutch, for example the clutch formed by clutch teeth 21, 61 of the dose dial sleeve 20 and the clutch sleeve 60. As an alternative, a relatively high force, e.g. exceeding the force of a clutch spring acting on clutch sleeve 60, may be required to actuate the axial switch 91. This results in actuation of the axial switch 91 during dose delivery operation or at the end of dose delivery.

Although not depicted in FIGS. 14 to 17, a second use signal may be generated during dose delivery, thereby turning on an encoder function of the electrical system. The generation of the second use signal may be identical or similar to the generation of the second use signal in the first to fourth embodiments, i.e. by interaction of a shuttle 50 with a ratchet 31, 32 of an encoder ring 30.

The electronic system 100 comprises an electronic control unit 110. The control unit may comprise a controller. Specifically, the control unit may comprise a processor arrangement. Also, the control unit 110 may comprise one, or a plurality of memory units, such as a program memory and a main memory. The control unit 110 is expediently designed to control operation of the electronic system 100. The control unit 110 may communicate via wired interfaces or wireless interfaces with further units of the electronic system 100. It may transmit signals containing commands and/or data to the units and/or receive signals and/or data from the respective unit. The connections between the units and the electronic control unit are symbolized by the lines in FIG. 18. However, there also may be connections between the units which are not illustrated explicitly. The control unit may be arranged on a conductor carrier, e.g. a (printed) circuit board, like the PCB 90 shown in FIGS. 14, 15 and 17. The other unit(s) of the electronic system may comprise one or more components which are arranged on the conductor carrier as well.

Electronic system 100 may further comprise a motion sensing unit 120. The motion sensing unit 120 may comprise one or a plurality of sensors, e.g. the sensor switches 42, 43, 44 described further above. In case optoelectronic sensors which detect electromagnetic radiation, such as IR sensors, are used, the motion sensing unit may additionally comprise a radiation emitter which emits the radiation to be detected by the sensor. However, it should be noted that other sensor systems, e.g. magnetic sensors could be employed as well. A motion sensing unit which has an electrically operated sensor and an electrically operated source for stimulating the sensor—such as a radiation emitter and an associated sensor—the power consumption may be particularly high and, hence, power management may have particular impact. Each sensor may have an associated radiation emitter. Motion sensing unit 120 may be designed to detect and preferably measure relative movement of two movable members of a dose setting and drive mechanism of or for the drug delivery device during a dose setting operation and/or during a dose dispensing operation. For example, the motion sensing unit may measure or detect relative rotational movement of two movable members of the dose setting and drive mechanism with respect to one another. Based on movement data received from or calculated from the signals of the unit 120, the control unit may calculate the dose data.

Electronic system 100 may further comprise a use detection unit 130. The use detection unit may be associated with the user interface member, e.g. button 11, or members such that manipulation of the member for setting and/or delivering a dose thereof may be detected. When the manipulation is detected, the use detection unit generates or triggers generation of a use signal. The use signal can be transmitted to the electronic control unit 110. The electronic control unit may, in response to the signal, issue a command or signal to one of, an arbitrarily selected plurality of, or all of the other electrically operated units of the system. For example, the control unit may cause that the respective unit is switched from a first state, e.g. a sleeping state or idle state with a lower power consumption or an off state with no power consumption, to a second state with an increased power consumption. The switching may be done by an according switching command or signal issued by the electronic control unit to the respective unit. In response to the use signal all units may be switched to the second state or just selected units. If only selected units are switched to the second state with higher power consumption, it is expedient that these units are intended to be used during the operation which is intended to be commenced by the user or which has been commenced.

The electronic system 100 may further comprise a communication unit 140, e.g. an RF, WiFi and/or Bluetooth unit. The communication unit may be provided as a communication interface between the system or the drug delivery device and the exterior, such as other electronic devices, e.g. mobile phones, personal computers, laptops and so on. For example, dose data may be transmitted by the communication unit to the external device. The dose data may be used for a dose log or dose history established in the external device. The communication unit may be provided for wireless or wired communication.

Electronic system may further comprise an electrical power supply 150, such as a rechargeable or non-rechargeable battery. The power supply 150 may provide electrical power to the respective units of the electronic system.

Although not explicitly depicted, the electronic system may comprise a, preferably permanent and/or non-volatile, storage or memory unit, which may store data related to the operation of the drug delivery device such as dose history data, for example.

Still further, in an embodiment the electrical use detection unit 130 may comprise a capacitive sensor instead of the axial switch 91.

Summarizing, according to the present disclosure the electrical use detection unit 130 may be able to detect contact to a face of the electronic system, e.g. the top face of an electronic module, meaning this system can be used to induce dose synchronisation with an app of a further electronic device, e.g. mobile phones, personal computers, laptops and so on, or to put the electronic module into a Bluetooth advertising mode. In the event that the dose button 11 was pressed (but no dose selected) for a time greater than $t_1$ (e.g. 1 second) but less than $t_2$ (e.g. 5 seconds) only one channel of the two IR-LEDs 92 would be observed to go to a "high" state. This characteristic signal could be used to initiate a dose synchronisation sequence with the app.

Similarly, if the dose button 11 was pressed (but no dose selected) for a time greater than $t_2$ (e.g. 5 seconds) the characteristic optical signal could be used to initiate a Bluetooth advertising sequence.

Thus, dose synchronisation and Bluetooth pairing may be achieved with the top-mounted switch 91 or other alternatives of the electrical use detection unit 130 as described above, if the switch is held closed for a specified period of time, e.g. 3-5 seconds to induce synchronization and/or more than 5 seconds to induce Bluetooth pairing.

| Reference Numerals | |
|---|---|
| 1 | device |
| 10 | housing |
| 11 | injection button |
| 12 | dosage knob |
| 13 | dosage window |
| 14 | container/container receptacle |
| 15 | needle |
| 16 | inner needle cap |
| 17 | outer needle cap |
| 18 | cap |
| 20 | dose dial sleeve |
| 21 | clutch teeth |
| 30 | encoder ring |
| 31 | ratchet teeth |
| 32 | ratchet pockets |
| 33 | transition ramp |
| 34 | cylindrical portion |
| 40 | chassis |
| 41 | guiding groove |
| 42 | electrical contact |
| 43 | electrical contact |
| 44 | electrical contact |
| 50 | shuttle (switching feature) |
| 51 | ratchet tooth |
| 52 | ramp |
| 60 | clutch sleeve |
| 61 | clutch teeth |
| 62 | flange-like protrusion |
| 70 | inner housing |
| 71 | proximal end face |
| 80 | pin |
| 81 | finger |
| 82 | ramp |
| 90 | PCB |
| 91 | axial switch |
| 92 | LED |
| 100 | electrical system |
| 110 | control unit |
| 120 | motion sensing unit |
| 130 | use detection unit |
| 140 | communication unit |
| 150 | electrical power supply |

The invention claimed is:

1. An electronic system for a drug delivery device, the electronic system comprising:

a dose setting and drive mechanism which is configured to perform a dose setting operation for setting a dose to be delivered by the drug delivery device and a dose delivery operation for delivering the set dose, the dose setting and drive mechanism comprising a first member and a second member, wherein the first member is a dial sleeve or is a member axially and/or rotationally locked to the dial sleeve such that the first member is rotatable relative to a housing of the dose setting and drive mechanism at least in the dose setting operation, and wherein the second member is a dose and/or injection button or a member axially and/or rotationally locked to the dose and/or injection button such that the second member is axially displaceable relative to the first member and rotationally constrained to the housing at least in the dose setting operation, wherein the dose setting and drive mechanism is configured such that, during at least one of the dose delivery operation or the dose setting operation, the first member moves relative to the second member;

a communication unit for communicating with an external device;

an electronic control unit configured to control an operation of the electronic system; and an electrical use detection unit operatively connected to the electronic control unit, and configured to generate a first signal indicative that a user has commenced or finished the relative movement between the first member and the second member, wherein the electronic system is configured to be switched from a first state in which the communication unit is not activated, into a second state in which the communication unit is activated, thereby inducing the communication unit to establish a communication with the external device, wherein the switching is in response to the first signal.

2. The electronic system according to claim 1, wherein the communication unit comprises a wireless communication interface for communicating with the external device, wherein the electronic system is configured to switch from the first state into the second state by the electronic control unit, thereby inducing the communication unit to initiate a manual synchronization and/or a pairing with the external device.

3. The electronic system according to claim 1, wherein the electrical use detection unit is further configured to generate a second signal indicative that the user has commenced the dose setting operation or the dose delivery operation, wherein the electronic system is configured to be switched from the first state or the second state into a third state by the electronic control unit in response to the second signal, wherein dose data is collected in the third state.

4. The electronic system according to claim 3, wherein the electrical use detection unit is configured to generate the second signal in response to a relative movement of the first member and the second member of the dose setting and drive mechanism.

5. The electronic system according to claim 3, wherein the electrical use detection unit is configured to generate the second signal in response to a relative rotational movement between a third member of the dose setting and drive mechanism, and one of the first member and the second member during the dose delivery operation.

6. The electronic system according to claim 1, further comprising a movable switching feature that is operatively coupled to one or both of the first member and the second member such that an axial displacement of the first member relative to the second member causes a movement of the switching feature relative to the first member and/or the second member, and wherein the electronic system is configured such that an axial movement of the switching feature is used to trigger generation of the first signal.

7. The electronic system according to claim 6, wherein the movable switching feature is linearly guided.

8. The electronic system according to claim 6, wherein the movable switching feature is resiliently biased into engagement with a block feature before the first member is moved axially a predefined distance relative to the second member, and wherein, when the first member is moved relative to the second member, the block feature is removed from the movable switching feature such to form a biasing force that drives the movement of the movable switching feature to cause the generation of the first signal.

9. The electronic system according to claim 1, further comprising a movable switching feature that is operatively coupled to the first member and/or the second member such that a predefined axial displacement of the first member relative to the second member is converted into a movement of the switching feature, the movement being perpendicular to the predefined axial displacement of the first member relative to the second member, and causing generation of the first signal.

10. The electronic system according to claim 9, wherein the predefined axial displacement is converted into the movement of the switching feature when the dose setting or dose delivery operation is finished.

11. The electronic system according to claim 1, wherein the electrical use detection unit comprises at least one electrically conductive spring arm deflectable in response to the relative movement between the first member and the second member to establish or break an electrical connection with at least one electrical contact, and wherein the electrical use detection unit is configured to generate the first signal in response to establishing or breaking an electrical connection between the at least one electrically conductive spring arm and the at least one electrical contact.

12. The electronic system according to claim 1, wherein the first member comprises an encoder ring having a first portion with a first inner diameter and a second portion with a second inner diameter different from the first inner diameter, wherein the first portion and the second portion are located at axially different positions of the encoder ring.

13. The electronic system according to claim 12, wherein a transition ramp is provided axially interposed between the first portion and the second portion.

14. The electronic system according to claim 12, wherein one of the first portion and the second portion is provided with a radially inwardly directed ratchet teeth and/or with ratchet pockets.

15. The electronic system according to claim 1, wherein the first member is a dial sleeve or is a member axially and/or rotationally locked to the dial sleeve such that first member is axially displaceable relative to a housing of the dose setting and drive mechanism at least in the dose delivery operation, and wherein the second member is a member axially displaceable relative to the first member upon abutment with the housing or a member axially locked to the first member at least in the dose delivery operation.

16. The electronic system according to claim 15, wherein the second member is guided in a dose and/or injection button or a member axially and/or rotationally locked to the dose and/or injection button such that the second member abuts the housing.

17. The electronic system according to claim 15, wherein the second member is a member axially locked to the dose and/or injection button only if the dose and/or injection button is axially displaced against a bias of a spring.

18. The electronic system according claim 1, wherein the dose and/or injection button is axially displaceable and/or axially elastically deformable relative to the first member, and wherein the electrical use detection unit comprises an axial switch such that an axial displacement of at least a portion of the dose and/or injection button relative to the first member actuates the axial switch.

19. A drug delivery device comprising:
a cartridge containing a medicament; and
an electronic system comprising
a dose setting and drive mechanism which is configured to perform a dose setting operation for setting a dose to be delivered by the drug delivery device and a dose delivery operation for delivering the set dose, the dose setting and drive mechanism comprising a first member and a second member,
wherein the first member is a dial sleeve or is a member axially and/or rotationally locked to the dial sleeve such that the first member is rotatable relative to a housing of the dose setting and drive mechanism at least in the dose setting operation, and wherein the second member is a dose and/or injection button or a member axially and/or rotationally locked to the dose and/or injection button such that the second member is axially displaceable relative to the first member and rotationally constrained to the housing at least in the dose setting operation,
wherein the dose setting and drive mechanism is configured such that, during at least one of the dose delivery operation the dose setting operation, the first member moves relative to the second member,
a communication unit for communicating with an external device,
an electronic control unit configured to control an operation of the electronic system,
an electrical use detection unit operatively connected to the electronic control unit, and configured to generate a first signal indicative that a user has commenced or finished the relative movement between the first member and the second member,
wherein the electronic control unit is configured to be switched from a first state in which the communication unit is not activated, into a second state in which the communication unit is activated, thereby inducing the communication unit to establish a communication with the external device, wherein the switching is in response to the first signal.

* * * * *